(12) United States Patent
Peng et al.

(10) Patent No.: US 7,815,816 B2
(45) Date of Patent: Oct. 19, 2010

(54) POLYFLUOROETHER-BASED PHOSPHATES

(75) Inventors: Sheng Peng, Hockessin, DE (US);
Stephen James Getty, Wilmington, DE (US); Xianjun Meng, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/691,292

(22) Filed: Jan. 21, 2010

(65) Prior Publication Data

US 2010/0129668 A1      May 27, 2010

Related U.S. Application Data

(62) Division of application No. 11/598,339, filed on Nov. 13, 2006, now Pat. No. 7,674,928.

(51) Int. Cl.
*D06M 15/667* (2006.01)
*D06M 15/00* (2006.01)

(52) U.S. Cl. .................. 252/8.62; 252/8.61; 427/384; 427/385.5; 427/389; 427/389.7; 427/389.9; 427/391; 427/393; 427/393.4; 427/393.6; 427/394; 427/395; 427/397

(58) Field of Classification Search ............. 252/8.61, 252/8.62; 427/384, 385.5, 389, 389.7, 389.9, 427/391, 393, 393.4, 393.6, 394, 395, 397
See application file for complete search history.

(56) References Cited

U.S. PATENT DOCUMENTS

| | | | |
|---|---|---|---|
| 3,293,306 A | 12/1966 | LeBleu et al. | |
| 3,492,374 A | 1/1970 | Bleu et al. | |
| 3,564,059 A | 2/1971 | Sianesi et al. | |
| 3,692,885 A * | 9/1972 | Anello et al. | 558/186 |
| 3,927,126 A | 12/1975 | Huber-Emden | |
| 4,499,146 A | 2/1985 | Piacenti et al. | |
| 5,011,713 A | 4/1991 | Lenti et al. | |
| 5,481,028 A | 1/1996 | Petrov et al. | |
| 5,563,213 A | 10/1996 | Mayer | |
| 6,184,187 B1 | 2/2001 | Howell et al. | |
| 6,271,289 B1 | 8/2001 | Longoria et al. | |
| 2006/0047032 A1 | 3/2006 | Miller et al. | |
| 2006/0047044 A1 | 3/2006 | Miller et al. | |

FOREIGN PATENT DOCUMENTS

| | | |
|---|---|---|
| EP | 1 238 004 B1 | 11/2000 |
| EP | 1 327 649 A2 | 7/2003 |
| JP | 06072936 | 3/1994 |
| JP | 1998251348 A | 9/1998 |
| JP | 2004189670 | 7/2004 |

OTHER PUBLICATIONS

Honda et al., Molecular aggregation structure and surface properties of poly(fluoroalkyl acrylate) thin films, Macromolecules, 2005, 38, 5699-5705.

* cited by examiner

*Primary Examiner*—Anthony J Green
(74) *Attorney, Agent, or Firm*—Nancy S. Mayer

(57) ABSTRACT

A composition comprising one or more compounds of formula (I) or (II):

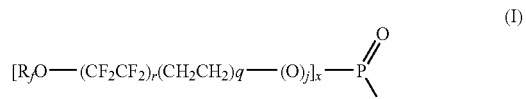

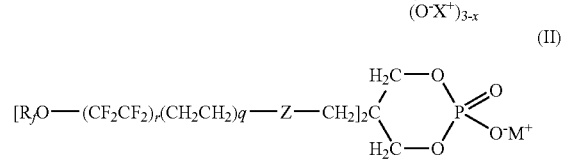

wherein:
$R_f$ is a linear or branched perfluoroalkyl having 1 to 7 carbon atoms, optionally interrupted by one to three oxygen atoms,
r and q are each independently an integer of 1 to 3,
j is 0 or 1, or a mixture thereof,
x is from about 1 to about 2,
Z is —O—, —S—, or —NR—,
R is hydrogen or an alkyl group containing 1 to 4 carbon atoms
X is hydrogen or M, and
M is an ammonium ion, an alkali metal ion, or an alkanolammonium ion, and its use in providing surface properties to substrates is disclosed.

9 Claims, No Drawings

POLYFLUOROETHER-BASED PHOSPHATES

CROSS-REFERENCE TO RELATED APPLICATION

This application is a divisional of Application No. 11/598,339 filed Nov. 13, 2006, and granted as U.S. Pat. No. 7,674,928 issued on Mar. 9, 2010.

FIELD OF THE INVENTION

This invention relates to the field of polyfluorinated compounds containing an ether linkage within the polyfluorinated chain, and particularly to such fluorophosphates, and to their use as surfactants and additives for coating compositions or as treatment agents to impart various surface properties to substrates.

BACKGROUND OF THE INVENTION

Polyfluorinated compositions are used in the preparation of a wide variety of surface treatment materials. These polyfluorinated compositions are typically made of perfluorinated carbon chains connected directly or indirectly to nonfluorinated functional groups capable of further reaction such as hydroxyl groups, carboxylic acid groups, halide groups and others. Various compositions made from perfluorinated compounds or polymers are known to be useful as surfactants or treating agents to provide surface effects to substrates. Surface effects include repellency to moisture, soil, and stains, and other effects, which are particularly useful for fibrous substrates and other substrates such as hard surfaces. Many such surfactants and treating agents are fluorinated polymers or copolymers.

Most commercially available fluorinated polymers useful as treating agents for imparting surface effects to substrates contain predominantly eight or more carbons in the perfluoroalkyl chain to provide the desired properties. Honda et al, in Macromolecules, 2005, 38, 5699-5705 teach that for perfluoroalkyl chains of greater than 8 carbons, orientation of the perfluoroalkyl groups, designated $R_f$ groups, is maintained in a parallel configuration while for such chains having less than 6 carbons, reorientation occurs. This reorientation decreases surface properties such as contact angle. Thus polymers containing shorter chain perfluoroalkyls have traditionally not been successful commercially for providing surface properties to treated substrates.

EP 1 238 004 (Longoria et al.) discloses a mixture of a fluoroalkyl phosphate and a fluoroacrylate polymer for use in providing stain resistance to stone, masonry, and other hard surfaces.

It is desirable to improve particular surface effects and to increase the fluorine efficiency; i.e., boost the efficiency or performance of treating agents so that lesser amounts of the expensive fluorinated composition are required to achieve the same level of performance, or so that better performance is achieved using the same level of fluorine. It is desirable to reduce the chain length of the perfluoroalkyl groups thereby reducing the amount of fluorine present, while still achieving the same or superior surface effects.

There is a need for compositions which significantly improve the repellency and stain resistance of fluorinated treating agents for substrates while using lower levels of fluorine. There is also a need for polymer compositions useful as additives in coatings, such as paints, stains, or clear coats, to provide resistance to blocking and enhanced open time extension. The present invention provides such compositions.

SUMMARY OF THE INVENTION

The present invention comprises a composition comprising one or more compounds of formula (I) or (II):

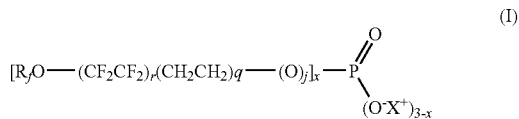

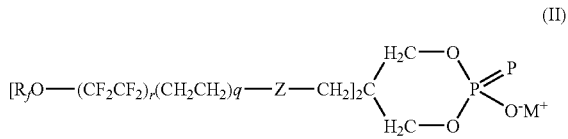

wherein:

$R_f$ is a linear or branched perfluoroalkyl having one to seven carbon atoms, optionally interrupted by one to three oxygen atoms, r and q are each independently an integer of 1 to 3, j is 0 or 1, or a mixture thereof, x is from about 1 to about 2, Z is —O—, —S—, or —NR—, R is hydrogen or an alkyl group containing 1 to 4 carbon atoms, X is hydrogen or M, and M is an ammonium ion, an alkali metal ion, or an alkanolammonium ion.

The present invention further comprises a method of providing water repellency, oil repellency and stain resistance to a substrate comprising contacting the substrate with the above described formula (I) or (II) or mixtures thereof.

The present invention further comprises a method of providing oil repellency, resistance to blocking, and open time extension to a substrate having deposited thereon a coating composition comprising addition to the coating composition prior to deposition on the substrate of a composition of the above described formula (I) or (II) or mixtures thereof.

The present invention further comprises a substrate to which has been applied a composition of the above described formula (I) or (II) or a mixture thereof, or a coating composition containing the above described formula (I) or (II) or a mixture thereof.

DETAILED DESCRIPTION OF THE INVENTION

Hereinafter trademarks are designated by upper case.

This invention comprises compositions of formula (I) and (II) as described above containing an ether linkage within the polyfluorinated chain designated $R_f$. The compositions are useful for contributing surface protection properties to paper, tiles, stone and other hard surfaced substrates. The compositions are also useful as surfactants, and as additives to coating compositions to provide surface-modifying properties to substrates coated therewith.

While, for simplicity, this invention will generally refer to the above compositions as fluoroalkylphosphates, it is to be recognized that one skilled in the art can readily apply this invention to other phosphorus derivatives of the fluoroalcohols and fluorothiols such as the corresponding fluoroalkylphosphites or fluoroalkylphosphinates. The present invention includes such fluoroalkylphosphites and fluoroalkylphosphinates. Similarly, while this invention salts will generally refer to the fluoroalkylphosphate salts as amine salts, it is to be recognized that that one skilled in the art can readily apply this invention to the corresponding ammonium or alkali metal salts, which are included within the invention.

The present invention comprises a composition comprising compounds of formula (I) or (II) or mixture thereof as described above.

In the compositions of the present invention $R_f$ is preferably a linear perfluoroalkyl group having one to six carbon atoms, more preferably one to four carbon atoms, and more preferably one to three carbon atoms. Preferred are compositions of formula (I) wherein r and q are 1, and X is ammonium.

The fluoroalcohols used as starting materials to make the compositions of the present invention are available by the following series of reactions:

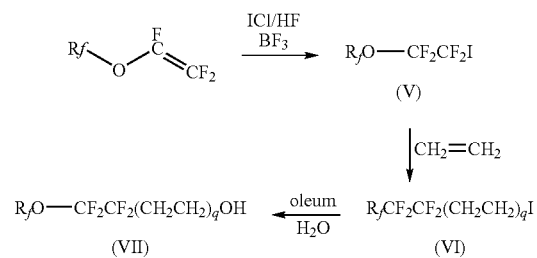

The starting perfluoroalkyl ether iodides of formula (V) above can be made by the procedure described in U.S. Pat. No. 5,481,028, herein incorporated by reference, in Example 8, which discloses the preparation of compounds of formula (V) from perfluoro-n-propyl vinyl ether.

In the second reaction above, a perfluoroalkyl ether iodide (V) is reacted with an excess of ethylene at an elevated temperature and pressure. While the addition of ethylene can be carried out thermally, the use of a suitable catalyst is preferred. Preferably the catalyst is a peroxide catalyst such as benzoyl peroxide, isobutyryl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time can vary with the catalyst and reaction conditions, but 24 hours is usually adequate. The product is purified by any means that separates unreacted starting material from the final product, but distillation is preferred. Satisfactory yields up to 80% of theory have been obtained using about 2.7 mols of ethylene per mole of perfluoroalkyl ether iodide, a temperature of 110° C. and autogenous pressure, a reaction time of 24 hours, and purifying the product by distillation.

The perfluoroalkylether ethylene iodides (VI) are treated with oleum and hydrolyzed to provide the corresponding alcohols (VII) according to procedures disclosed in WO 95/11877 (Elf Atochem S.A.). Alternatively, the perfluoroalkylether ethyl iodides can be treated with N-methyl formamide followed by ethyl alcohol/acid hydrolysis. A temperature of about 130° to 160° C. is preferred. The higher homologs (q=2, 3) of telomer ethylene iodides (VI) are available with excess ethylene at high pressure.

The telomer ethylene iodides (VI) are treated with a variety of reagents to provide the corresponding thiols according to procedures described in J. Fluorine Chemistry, 104, 2 173-183 (2000). One example is the reaction of the telomer ethylene iodides (VI) with sodium thioacetate, followed by hydrolysis. The telomer ethylene iodide (VI) can also be treated to provide the corresponding thioethanols or thioethylamines by conventional methods.

Specific fluoroether alcohols useful in forming compounds of the invention include those listed in Table 1A, and specific fluoroether thiols useful in forming compounds of the invention include those in Table 1B. The groups $C_3F_7$, $C_4F_9$, and $C_6F_{13}$, referred to in the list of specific alcohols and thiols in Tables 1A and 1B, refer to linear perfluoroalkyl groups unless specifically indicated otherwise.

TABLE 1A $F_3COCF_2CF_2CH_2CH_2OH$,
$F_3CO(CF_2CF_2)_2CH_2CH_2OH$,
$C_2F_5OCF_2CF_2CH_2CH_2OH$,
$C_2F_5O(CF_2CF_2)_2CH_2CH_2OH$,
$C_3F_7OCF_2CF_2CH_2CH_2OH$,
$C_3F_7O(CF_2CF_2)_2CH_2CH_2OH$,
$C_4F_9OCF_2CF_2CH_2CH_2OH$,
$C_4F_9O(CF_2CF_2)_2CH_2CH_2OH$,
$C_6F_{13}OCF_2CF_2CH_2CH_2OH$,
$C_6F_{13}O(CF_2CF_2)_2CH_2CH_2OH$,
$F_3COCF(CF_3)CF_2OCF_2CF_2CH_2CH_2OH$,
$F_3COCF(CF_3)CF_2O(CF_2CF_2)_2CH_2CH_2OH$,
$C_2F_5OCF(CF_3)CF_2OCF_2CF_2CH_2CH_2OH$,
$C_2F_5OCF(CF_3)CF_2O(CF_2CF_2)_2CH_2CH_2OH$,
$C_3F_7OCF(CF_3)CF_2OCF_2CF_2CH_2CH_2OH$,
$C_3F_7OCF(CF_3)CF_2O(CF_2CF_2)_2CH_2CH_2OH$,

TABLE 1B $F_3COCF_2CF_2CH_2CH_2SH$,
$F_3CO(CF_2CF_2)_2CH_2CH_2SH$,
$C_2F_5OCF_2CF_2CH_2CH_2SH$,
$C_2F_5O(CF_2CF_2)_2CH_2CH_2SH$,
$C_3F_7OCF_2CF_2CH_2CH_2SH$,
$C_3F_7O(CF_2CF_2)_2CH_2CH_2SH$,
$C_4F_9OCF_2CF_2CH_2CH_2SH$,
$C_4F_9O(CF_2CF_2)_2CH_2CH_2SH$,
$C_6F_{13}OCF_2CF_2CH_2CH_2SH$,
$C_6F_{13}O(CF_2CF_2)_2CH_2CH_2SH$,
$F_3COCF(CF_3)CF_2OCF_2CF_2CH_2CH_2SH$,
$F_3COCF(CF_3)CF_2O(CF_2CF_2)_2CH_2CH_2SH$,
$C_2F_5OCF(CF_3)CF_2OCF_2CF_2CH_2CH_2SH$,
$C_2F_5OCF(CF_3)CF_2O(CF_2CF_2)_2CH_2CH_2SH$,
$C_3F_7OCF(CF_3)CF_2OCF_2CF_2CH_2CH_2SH$,
$C_3F_7OCF(CF_3)CF_2O(CF_2CF_2)_2CH_2CH_2SH$

The compositions of formula (I) and (II) of the present invention are prepared according to the method described by Longoria et al in U.S. Pat. No. 6,271,289, and Brace and Mackenzie, in U.S. Pat. No. 3,083,224 each herein incorporated by reference. Typically, either phosphorus pentoxide ($P_2O_5$) or phosphorus oxychloride ($POCl_3$) is reacted with a fluoroalcohol or fluorothiol to give mixtures of the mono- and bis(perfluoroalkyl)phosphoric acids. Neutralization, using common bases such as ammonium, sodium hydroxide, or an amine provides the corresponding phosphates. Reacting an excess of fluoroalcohol or fluorothiol with $P_2O_5$ followed by neutralization provides a mixture of mono(perfluoroalkyl) phosphate and bis(perfluoroalkyl)phosphate. Higher ratios of bis(perfluoroalkyl)phosphate to mono(perfluoroalkyl)phosphate are obtained by using the method of Hayashi and Kawakami in U.S. Pat. No. 4,145,382. The phosphite and phosphinate compositions are prepared in the same manner.

The resulting composition is then diluted with water, mixture of water and solvent, or further dispersed or dissolved in a solvent selected from the groups comprising simple alcohols and ketones that are suitable as the solvent for final application to substrates (hereinafter the "application solvent"). Alternatively, an aqueous dispersion, made by conventional methods with surfactants, is prepared by removing solvents by evaporation and the use of emulsification or homogenization procedures known to those skilled in the art. Such solvent-free emulsions may be preferred to minimize flammability and volatile organic compounds (VOC). The final product for application to a substrate is a dispersion (if water based) or a solution (if solvents other than water are used).

It will be apparent to one skilled in the art that many changes to any or all of the above procedures can also be used to optimize the reaction conditions for obtaining maximum yield, productivity or product quality.

The present invention comprises fluorinated aqueous mixtures comprising a mixture of an anionic aqueous fluoroalkyl phosphate (or phosphite or phosphonite) solution neutralized with a base, preferably an amine such as dialkanolamine base. The composition is neutralized to a pH of from about 5 to about 10, preferably from about 6 to about 9, more preferably from about 6 to about 8.

The various molar ratios of the fluoroalcohol or fluorothiol, acid, and base can be identified by the format (a:1:b): thus the (2:1:1) salt is, for example, the bis(fluoroalkyl) phosphate amine salt, the (1:1:2) salt is, for example, the fluoroalkylethyl phosphate bis(amine salt) and the (1:1:1) salt is, for example, the fluoroalkylethyl phosphate amine salt. Preferably the (2:1:1) salt is the bis(fluoroalkylethyl) phosphate diethanolamine salt, the (1:1:2) salt is the fluoroalkylethyl phosphate bis(diethanolamine salt) and the (1:1:1) salt is the fluoroalkylethyl phosphate diethanolamine salt. The salts of the fluoroalkylphosphates are preferred over the corresponding acids by reason of their increased water solubility.

The salts of the fluoroalkylphosphates are preferred over the corresponding acids as outlined in U.S. Pat. No. 3,083,224 by reason of their increased water solubility.

The present invention further comprises a method of providing water repellency, oil repellency, and stain resistance to a substrate comprising contacting the substrate with a composition of formula (I) or (II) as defined above, or a mixture thereof. The composition of the present invention is typically applied by contacting the substrate with the composition by conventional means, including but not limited to, brush, spray, roller, doctor blade, wipe, immersion, dip techniques, foam, liquid injection, casting, and the like. Optionally, more than one application can be used, particularly on porous surfaces.

When used on stone, tile and other hard surfaces, the compositions of the invention are typically diluted with water to give an application solution having about 0.1 weight % to about 20 weight %, preferably from about 1.0 weight % to about 10 weight %, and most preferably from about 2.0 weight % to about 5.0 weight %, of the composition based on solids. The coverage as applied to a substrate is about 100 g of application solution per sq meter ($g/m^2$) for semi-porous substrates (e.g. limestone) and 200 $g/m^2$ for porous substrates (e.g. saltillo). Preferably the application results in about 0.1 $g/m^2$ to about 2.0 $g/m^2$ of solids being applied to the surface.

When used as a surface treatment for paper, the compositions of the invention are typically diluted with water to give an application solution having about 0.01 to about 20 weight %, preferably about 0.1 weight % to about 10 weight %, and most preferably about 0.5 weight % to about 5 weight %, of the composition based on solids. The coverage as applied to paper is about 10 $g/m^2$ to about 200 $g/m^2$, and preferably about 10 $g/m^2$ to about 200 $g/m^2$ of the application solution. Preferably the application results in about 0.1 $g/m^2$ to about 5.0 $g/m^2$ of solids being applied to the paper.

The compositions of the present invention are also used as an additive during the manufacture of substrates. They are added at any suitable point during manufacture. For example, in the case of paper, they are added to the paper pulp in a size press. The amount added is from about 0.3% to about 0.5% by weight based on dry fluorochemical solids on dry paper fiber.

The composition of this invention is applied to or contacted with the substrate as such, or in combination with one or more other finishes or surface treating agents. The composition of the present invention optionally further comprises additional components such as treating agents or finishes to achieve additional surface effects, or additives commonly used with such agents or finishes. Such additional components comprise compounds or compositions that provide surface effects such as stain repellency, stain release, soil repellency, soil release, water repellency, oil repellency, odor control, antimicrobial, sun protection, and similar effects. One or more of such treating agents or finishes can be blended with the composition of the present invention and applied to the substrate.

Other additives commonly used with such treating agents or finishes can also be present such as surfactants, pH adjusters, leveling agent, wetting agents, and other additives known by those skilled in the art. Examples of such finishes or agents include processing aids, foaming agents, lubricants, antistains, and the like. The composition is applied at a manufacturing facility, retailer location, or prior to installation and use, or at a consumer location.

The present invention further comprises a method of providing resistance to blocking, open time extension and oil repellency to a substrate having deposited thereon a coating composition comprising adding to the coating composition prior to deposition on the substrate of a composition comprising one or more compounds of formula (I) or (II) as described above, or a mixture thereof. The compounds are employed as additives to the coating composition, and are added and mixed into the composition. Suitable coating compositions, referred to herein by the term "coating base", include typical paints, stains, and clear coats, usually a liquid formulation, of an alkyd coating, Type I urethane coating, unsaturated polyester coating, or water-dispersed coating. Such coating compositions are applied to a substrate for the purpose of creating a lasting film on the substrate surface.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. In order that curing can take place at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

The term "open time extension" is used herein to mean the time during which a layer of liquid coating composition can be blended into an adjacent layer of liquid coating composition without showing a lap mark, brush mark, or other application mark. It is also called wet-edge time. Latex paint containing low boiling volatile organic chemicals (VOC) has shorter than desired open-time due to lack of high boiling temperature VOC solvents. Lack of open time extension will cause surface defects such as overlapping brush marks or other marks. A longer open time extension is beneficial when the appearance of the coated surface is important, as it permits application of the coating without leaving overlap marks, brush marks, or other application marks at the area of overlap between one layer of the coating and an adjacent layer of the coating.

When used as additives the compositions of the present invention are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition.

When used as an additive to a coating base, the compositions of the invention generally are added at about 0.001 weight % to about 5 weight % based on solids (by weight based on solids of the additive in the paint). Preferably about 0.01 weight % to about 1 weight %, and more preferably 0.1 weight % to about 0.5 weight % is used.

The present invention also comprises substrates treated with the composition of the present invention. Suitable substrates include fibrous or hard surface substrates. The fibrous substrates include wood, paper, and leather. The hard surface substrates include porous and non-porous mineral surfaces, such as glass, stone, masonry, concrete, unglazed tile, brick, porous clay and various other substrates with surface porosity. Specific examples of such substrates include unglazed concrete, brick, tile, stone, granite, limestone, marble, grout, mortar, statuary, monuments, wood, composite materials such as terrazzo, and wall and ceiling panels including those fabricated with gypsum board. These are used in the construction of buildings, roads, parking ramps, driveways, floorings, fireplaces, fireplace hearths, counter tops, and other decorative uses in interior and exterior applications.

The compositions of the present invention are useful to provide one or more of water repellency, oil repellency, and stain resistance to treated substrates. The compositions of the present invention are also useful to provide oil repellency, resistance to blocking, and open time extension to substrates coated with a coating composition to which the composition of the present invention has been added. These properties are obtained using lower fluorine concentrations compared with conventional perfluorocarbon surface treatment agents, providing improved "fluorine efficiency" in the protection of treated surfaces. The compositions of the present invention are effective at fluorine concentrations about one half to one third of the fluorine concentration for conventional fluorochemical surface protectants. The compositions of the present invention also allow for the use of shorter fluoroalkyl groups containing 7 or fewer carbon atoms while conventional commercially available surface treatment products typically show poor oil repellency and water repellency performance if the fluoroalkyl groups contain less 8 carbon atoms.

Test Methods

The following test methods were used in the Examples herein.

Test Method 1—Repellency for Paper

The oil repellency of paper samples were tested by using the AATCC Kit Test Procedure (118-1997). Each test specimen was placed on a clean flat surface, test side up, being careful not to touch the area to be tested. From a height of about one inch (2.5 cm), a drop of test solution from an intermediate Kit Number testing bottle was dropped onto the test area. A stop watch was started as the drop was applied. After exactly 15 seconds, the excess fluid was removed with a clean swatch of cotton tissue and the wetted area was immediately examined. Failure was evidenced by a pronounced darkening of the specimen caused by penetration, even in a small area, under the drop. The procedure was repeated as required, making sure that drops from other Kit Number bottles fell in untouched areas. The Results were reported as the Kit Rating, which was the highest numbered solution that stood on the surface of the specimen for 15 seconds without causing failure. Thus higher numbers indicate superior performance. The average Kit Rating of five specimens to the nearest 0.5 number was reported.

TABLE 1

The composition of AATCC Kit test solution (Tappi Kit Test Solution)

| Rating Number | Composition Results |
|---|---|
| 0 | The test sample fails Kaydol* |
| 1 | Passes Kaydol* |
| 2 | Passes 65:35 (v/v) Kaydol:n-hexadecane |
| 3 | Passes n-hexadecane |
| 4 | Passes n-tetradecane |
| 5 | Passes n-dodecane |
| 6 | Passes n-decane |
| 7 | Passes n-octane |
| 8 | Passes n-heptane |

*Kaydol is a light mineral oil available from Psaltz & Bauer, Inc., Waterbury, CT.

Test Method 2—Blocking Resistance of Architectural Latex Paints

The test method described herein is a modification of ASTM D4946-89—Standard Test Method for Blocking Resistance of Architectural Paints, which is hereby specifically incorporated by reference.

The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using an applicator blade. All painted panels were protected from grease, oil, fingerprints, dust, et cetera, to avoid surface contamination that could affect blocking resistance results. Typically, results are evaluated at 24 hours after casting the paint. After the panels have been conditioned in the conditioned room as specified in the ASTM Method referenced above for the desired period of time, six squares (3.8 cm×3.8 cm) were cut out from the painted test panel. The cut sections (three pairs) were placed with the paint surfaces face-to-face for each of the paints to be tested. The cut sections (three pairs) are placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi ($12.4 \times 10^3$ Pa) on the specimens. One weight and stopper was used for each specimen tested. After exactly 30 minutes, the stoppers and weights were taken off the test specimens which were removed from the oven and allowed to cool in the conditioned room for 30 minutes before determining resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in Table 1. The degree of seal was estimated from the appearance of the specimens and the fraction of the paint surfaces that adhere. Paint tearing away from the test panel backing was an indication of seal. A higher number indicates better resistance to blocking.

TABLE 2

Blocking Resistance Numerical Ratings

| Blocking Resistance Numerical Ratings | Description of the Separation | Performance Description |
|---|---|---|
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky - no seal | Poor to fair |
| 3 | 5 to 25% seal | Poor |
| 2 | 25 to 50% seal | Poor |
| 1 | 50 to 75% seal | Very poor |
| 0 | 75 to 100% seal | Very poor |

Test Method 3—Surface Tension Measurement

Surface tension is measured using a Kruess Tensiometer, K11 Version 2.501 in accordance with instructions with the equipment. The Wilhelmy Plate method is used. A vertical plate of known perimeter is attached to a balance, and the force due to wetting is measured. 10 replicates are tested of each dilution, and the following machine settings are used:

Method: Plate Method SFT
Interval: 1.0 s
Wetted length: 40.2 mm
Reading limit: 10
Min Standard Deviation: 2 dynes/cm
Gr. Acc.: 9.80665 m/s^2

Test Method 4—Contact Angle Measurement

Contact angles are measured by the Sessile prop Method, which is described by A. W. Adamson in The Physical Chemistry of Surfaces, Fifth Edition, Wiley & Sons, New York, N.Y., 1990. Additional information on the equipment and procedure for measuring contact angles is provided by R. H. Dettre et al. in "Wettability", Ed. by J. C. Berg, Marcel Dekker, New York, N.Y., 1993.

In the Sessile prop Method, a Ramè-Hart optical bench (available from Ramè-Hart Inc., 43 Bloomfield Ave., Mountain Lakes, N.J.) is used to hold the substrate in the horizontal position. The contact angle is measured at a prescribed temperature with a telescoping goniometer from the same manufacturer. A drop of test liquid is placed on a polyester scrub test panel (Leneta P-121 dull black or equivalent, Leneta Company, Mahwah, N.J.) and the tangent is precisely determined at the point of contact between the drop and the surface. An advancing angle is determined by increasing the size of the drop of liquid and a receding angle is determined by decreasing the size of the drop of liquid. The data are presented typically as advancing and receding contact angles.

The relationship between water and organic liquid contact angles, and the cleanability and dirt retention of surfaces is described by A. W. Adamson, above. In general, higher hexadecane contact angles indicate that a surface has greater dirt and soil repellency, and easier surface cleanability.

The water and hexadecane advancing angles of the dried coating compositions containing a composition of the present invention as an additive were measured on coatings cast on the Leneta panels, available from The Leneta Company, Mahwah, N.J.

Test Method 5—Open-Time Extension

Open-time is time during which a layer of applied liquid coating composition can be blended into an adjacent layer of liquid coating composition without showing a lapmark, brush mark, or other application mark. It is also called wet-edge time. Low VOC latex paint has shorter than desired open-time due to lack of high boiling temperature VOC solvents. Lack of sufficient open-time will result in overlapping brush marks or other marks. Open-time testing is conducted by a well accepted industry practice, called thumb press method as described herein. A double strip drawn down panel of the control sample and the sample with 0.1% active ingredient of the sample to be tested are employed. The coating composition to be tested and the control are the same coating composition wherein the control contains no additive to be tested, and the sample to be tested contains a composition of the present invention as an additive. The panel is made with a 7 cm doctor blade at 20-25° C. and 40-60% relative humidity. A double thumb press with equal pressure is then applied to each sample side by side at 1-2 minute intervals. The end point is when no paint residue on the thumb is observed. The time from when the drawdown is made to the end point is recorded as open-time. The percent difference between the control and the sample containing a composition of the present invention as an additive is recorded as the percent open-time extension. Compositions of the present invention were tested in a semi-gloss latex paint and a matte finish paint.

Test Method 6—Determination of Water and Oil Repellency

This test method describes the procedure for testing water repellency on hard surface substrates including limestone, concrete, granite, and saltillo. Square tiles of 12 inch square (30.5 cm$^2$) of a sample limestone (Euro Beige), and granite (White cashmere) were cut into 4 inch (10.2 cm) by 12 inch (30.5 cm) samples. Concrete bricks employed were 7.5 inch (19 cm) by 3.5 inch (9 cm), and saltillo pavers employed were 12-inch square (30.5 cm$^2$) were employed. After cutting, the samples were rinsed to remove any dust or dirt and allowed to dry thoroughly, typically for at least 24 hours. A penetrating solution was prepared by mixing a composition of the present invention with deionized water, with mixing, to provide a fluorine concentration of 0.8% fluorine by weight. A ½-inch (1.3 cm) paintbrush was used to apply the solution to samples of each substrate surface. The surface was then allowed to dry for fifteen minutes. If necessary, the surface was wiped with a cloth soaked in the treating solution to remove any excess. After the treated substrates dried overnight, three drops of deionized water and three drops of Canola oil were placed on each substrate and allowed to sit for five minutes. Visual contact angle measurements were used to determine water and oil repellency. The following rating chart was used to determine contact angle using a 0 to 5 scale, as shown below:

Repellency Rating 5 (Excellent): Contact angle 100°-120°.
Repellency Rating 4 (Very good): Contact angle 75°-90°.
Repellency Rating 3 (Good): Contact angle 45°-75°.
Repellency Rating 2 (Fair): Contact angle 25°-45°.
Repellency Rating 1 (Poor): Contact angle 10°-25°.
Repellency Rating 0 (Penetration): Contact angle<10°.

Higher numbers indicate greater repellency with ratings of 2 to 5 being acceptable. The data is reported in the tables as water beading and oil beading.

Test Method 7—Determination of Stain Resistance

Stain resistance was determined on limestone, concrete and Saltillo substrates using this method. Square tiles of 12 inch square (30.5 cm$^2$) of a sample limestone (Euro Beige) were cut into 4 inch (10.2 cm) by 12 inch (30.5 cm) samples. Concrete bricks employed were 7.5 inch (19 cm) by 3.5 inch (9 cm), and saltillo pavers employed were 12-inch square (30.5 cm$^2$) were employed. After cutting, the samples were rinsed to remove any dust or dirt and allowed to dry thoroughly, typically for at least 24 hours. A penetrating solution was prepared by mixing the composition of the present invention with deionized water to provide a concentration of 0.8% fluorine by weight. A ½-inch (1.3 cm) paintbrush was used to apply the solution to samples of each substrate surface. The surface was then allowed to dry for fifteen minutes. If necessary, the surface was wiped with a cloth soaked in the treating solution to remove any excess. After the treated substrates dried overnight, the following food stains were placed at intervals on the surface of the substrate: 1) hot bacon grease, 2) cola, 3) black coffee, 4) grape juice, 5) Italian salad dressing, 6) ketchup, 7) lemon juice, 8) mustard, 9) canola oil and 10) motor oil. After a 24-hour period, the food stains were blotted or lightly scraped from the substrate surface. The substrate's surface was rinsed with water and a 1% soap solution, and a stiff bristle brush was used to scrub the surface 10 cycles back and forth. The substrates were then rinsed with water and allowed to dry for 24 hours before rating.

The stains remaining on the tile surfaces after cleaning were rated visually according to a scale of 0 to 4 as follows: 0=no stain; 1=very light stain; 2=light stain; 3=moderate stain; and 4=heavy stain. The ratings for each substrate type are summed for each of the stains to give a composite rating for each type. The maximum total score for one substrate was 10 stains times the maximum score of 4=40. Lower scores indicated better stain protection, with scores of 20 or less being acceptable and with zero indicating the best protection with no stain present.

EXAMPLES

Example 1

$C_3F_7OCF_2CF_2I$ (100 g, 0.24 mol) and benzoyl peroxide (3 g) were charged under nitrogen into a vessel. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg pressure (3325 Pa).

A mixture of $C_3F_7OCF_2CF_2CH_2CH_2I$ (300 g, 0.68 mol) and N-methyl-formamide (300 mL), was heated to 150° C. for 26 hours. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of $C_3F_7OCF_2CF_2CH_2CH_2OH$ in 85% yield. The boiling point is 71~73° C. at 40 mmHg (5320 Pa).

Phosphorous pentoxide (2.87 g) (0.02 mols) was added to 20 g (0.06 mols) of $C_3F_7OCF_2CF_2CH_2CH_2OH$ at 85° C. and the reaction was heated to 100° C. After 16 hours, 34 mL of isopropyl alcohol was added to the reaction mixture at 85° C., stirred for 30 minutes, followed by the addition of 43 mL of DI water. After 1.5 hours, 5.93 mL (0.06 mols) of diethanolamine was added and the reaction was stirred for 2 hours at 65° C. to provide the diethanolamine salt of the resulting polyfluoropolyether-based phosphate of formula (I) wherein j, q, and r were each 1, $R_f$ was n-$C_3F_7$.

The resulting product was applied to paper samples (white bleached 50# paper) for oil repellency testing using Test Method 1. Results are in Table 3. A penetrating solution was prepared containing a fluorine concentration of 0.8% fluorine by weight and was applied to limestone and concrete substrates as described in Test Methods 6 and 7. The substrate samples and untreated controls were tested for water repellency, oil repellency and stain resistance according to Test Methods 6 and 7. The test results are shown in Tables 4 and 5.

The product of this example was also tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Tables 13A and 13B.

Example 2

$C_2F_5OCF_2CF_2I$ (116 g, 0.32 mol) and benzoyl peroxide (4 g) were charged under nitrogen into a vessel. A series of three vacuum/N2 gas sequences was then executed at −50° C. and ethylene (24 g, 0.86 mol) was introduced. The vessel was heated for 24 hour at 110° C. The autoclave was cooled to 0° C. and opened after degassing. Then the product was collected in a bottle. Six runs were combined, and the product was distilled giving 470 g of $C_2F_5OCF_2CF_2CH_2CH_2I$ in 64% yield. The boiling point was 75~77° C. at 25 mm Hg pressure (3325 Pa).

The flask was charged with 130 g of $C_2F_5OCF_2CF_2CH_2CH_2I$, 643 mL of the methylpyrrolidinone and 48 mL of deionized (DI) water. The reaction mixture was heated to 132 C for 20 hours. DI water was added and the lower layer was separated. The lower layer was dissolved in ether, washed with saturated sodium sulfite, and dried over anhydrous sodium sulfate. After rotary vaporization, 48 g of $C_2F_5OCF_2CF_2CH_2CH_2OH$ was obtained by distillation in 52% yield. The boiling point was 70~72° C. at 60 mm Hg pressure (7980 Pa).

Phosphorous pentoxide (1.70 g) (0.012 mols) was added to 10 g (0.036 mols) of the $C_2F_5OCF_2CF_2CH_2CH_2OH$ at 85° C. and reaction was heated to 100° C. After 16 hours, 20 mL of isopropyl alcohol was added to the reaction mixture at 85° C. stirred for 30 minutes, followed by the addition of 25.5 mL of DI water. After 1.5 hours, 3.86 g of diethanolamine was added and the reaction was stirred for 2 hours at 65° C. to provide the diethanolamine salt of the resulting polyfluoropolyether-based phosphate of formula (I) wherein j, q and r were each 1, $R_f$ was $C_2F_5$.

The resulting product was applied to paper samples (white bleached 50# paper) for oil repellency testing using Test Method 1. Results are in Table 3. A penetrating solution was prepared containing a fluorine concentration of 0.8% fluorine by weight and was applied to limestone and concrete substrates as described in Test Methods 6 and 7. The substrate samples and untreated controls were tested for water repellency, oil repellency and stain resistance according to Test Methods 6 and 7. The test results are shown in Tables 4 and 5.

The product of this example was also tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Example 3

$CF_3OCF_2CF_2I$ (285 g, 0.91 mol) and benzoyl peroxide (12 g) were charged under nitrogen into a vessel. A series of three vacuum/nitrogen gas sequences were then executed at −50° C., after which ethylene (69 g, 2.46 mol) was introduced. The vessel was heated for 24 hours at 110° C. The autoclave was cooled to 0° C. and opened after degassing. Then the product was collected in a bottle. Two runs were combined and the product was distilled giving 292 g of $CF_3OCF_2CF_2CH_2CH_2I$ in 50% yield. The boiling point of the product was 56~60° C. at 60 mmHg pressure (7980 Pa).

A mixture of $CF_3OCF_2CF_2CH_2CH_2I$, (92 g, 0.27 mol) and N-methyl-formamide (119 mL), was heated to 150° C. for 26 hours. Then the reaction was cooled to 100° C., followed by the addition of water to separate the crude ester. Ethyl alcohol (30 mL) and p-toluene sulfonic acid (1.03 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 44 g of $CF_3OCF_2CF_2CH_2CH_2OH$ in 71% yield.

Phosphorous pentoxide (2.06 g) (0.0145 mols) was added to 10 g (0.0435 mols) of $CF_3OCF_2CF_2CH_2CH_2OH$ at 85° C. and the reaction was heated to 100° C. After 16 hours, 34 mL of isopropyl alcohol was added to the reaction mixture at 85° C., stirred for 30 minutes, followed by the addition of 31 mL of DI water. After 1.5 hours, 4.67 g (0.044 mols) DEA was added and the reaction was stirred for 2 hours at 65° C. to provide the diethanolamine salt of the resulting polyfluoropolyether-based phosphate of formula (I) wherein j, q and r were each 1, $R_f$ was $CF_3$.

The resulting product was applied to paper samples (white bleached 50# paper) for oil repellency testing using Test Method 1. Results are in Table 3. A penetrating solution was prepared containing a fluorine concentration of 0.8% fluorine by weight and was applied to limestone and concrete substrates as described in Test Methods 6 and 7. The substrate samples and untreated controls were tested for water repellency, oil repellency and stain resistance according to Test Methods 6 and 7. The test results are shown in Tables 4 and 5. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Comparative Example A

The procedure of Example 1 was employed, but using the same equivalents of a fluorochemical prepared from a perfluoroalkylethyl alcohol mixture of the formula $F(CF_2)_a CH_2CH_2OH$, with and average molecular weight of 471 wherein a ranged from 6 to 14, and was predominately 6, 8, and 10. The typical mixture was as follows: 27% to 37% of a=6, 28% to 32% of a=8, 14% to 20% of a=10, 8% to 13% of a=12, and 3% to 6% of a=14. This compound is commercially available from E. I. du Pont de Nemours and Company, Wilmington, Del. The resulting product was applied on paper samples and tested for oil repellency using Test Method 1 as in Example 1. Resulting data are in Table 3.

TABLE 3

Oil Repellency on Paper

| Example | Phosphate $g/m^2$ | Fluorine $g/m^2$ | Repellency |
|---|---|---|---|
| Untreated control | 0 | 0 | 0 |
| 1 | 0.293 | 0.133 | 4 |
| 2 | 0.293 | 0.122 | 2 |
| 3 | 0.293 | 0.111 | 2 |
| Comparative A | 0.293 | 0.155 | 3 |
| 1 | 0.586 | 0.265 | 5 |
| 2 | 0.586 | 0.244 | 5 |
| 3 | 0.586 | 0.222 | 4 |
| Comparative A | 0.586 | 0.308 | 5 |

The data in Table 3 demonstrates that the above Examples 1 to 3 provided excellent oil repellency when applied to a paper substrate. The repellency was comparable to Comparative Example A, but Examples 1 to 3 contained a lower level of fluorine to generate this performance.

TABLE 4

Tests Results on Limestone

| | Example | | | |
|---|---|---|---|---|
| | 1 | 2 | 3 | Control |
| % F in solution | 0.8 | 0.8 | 0.8 | 0 |
| Amount Applied ($g/m^2$) | 0.47 | 0.48 | 0.46 | 0 |
| Food stains | | | | |
| Coke | 1 | 1 | 2 | 3 |
| Mustard | 3 | 2 | 2 | 3 |

TABLE 4-continued

Tests Results on Limestone

| | Example | | | |
|---|---|---|---|---|
| | 1 | 2 | 3 | Control |
| Ketchup | 1 | 1 | 2 | 2 |
| Grape juice | 1 | 1 | 2 | 3 |
| Italian dressing | 1 | 2 | 1 | 3 |
| Coffee | 3 | 3 | 2 | 3 |
| Lemon Juice | 4 | 4 | 4 | 4 |
| Motor Oil | 1 | 1 | 1 | 4 |
| Canola Oil | 0 | 1 | 1 | 4 |
| Bacon Grease | 0 | 1 | 1 | 4 |
| Total | 15 | 17 | 18 | 33 |
| Water Beading | 2 | 2 | 2 | 1 |
| Oil Beading | 4 | 4 | 4 | 1 |

TABLE 5

Tests Results on Concrete

| | Example | | | |
|---|---|---|---|---|
| | 1 | 2 | 3 | Control |
| % F in solution | 0.8 | 0.8 | 0.8 | 0 |
| Amount Applied ($g/m^2$) | 3.37 | 3.22 | 3.25 | 0 |
| Food stains | | | | |
| Coke | 1 | 1 | 3 | 3 |
| Mustard | 2 | 3 | 2 | 4 |
| Ketchup | 1 | 1 | 1 | 4 |
| Grape juice | 2 | 3 | 3 | 4 |
| Italian dressing | 0 | 2 | 1 | 4 |
| Coffee | 2 | 2 | 3 | 3 |
| Lemon Juice | 3 | 3 | 2 | 3 |
| Motor Oil | 3 | 3 | 2 | 4 |
| Canola Oil | 3 | 2 | 2 | 4 |
| Bacon Grease | 4 | 4 | 3 | 4 |
| Total | 21 | 24 | 22 | 37 |
| Water Beading | 4 | 3 | 3 | 1 |
| Oil Beading | 4 | 4 | 4 | 0 |

The data in Tables 4 and 5 show improved resistance to staining for limestone and concrete treated with the composition of the present invention for Examples 1 to 3 for various food stains compared to an untreated control. Water repellency and oil repellency were also demonstrated and are noted in the Table as Oil Beading and Water Beading.

Example 4

Phosphorous pentoxide (1.87 g, 0.013 mols) was added to 10 g (0.03 mols) of $C_3F_7OCF_2CF_2CH_2CH_2OH$ prepared as in Example 1 at 85° C. and reaction was heated to 100° C. After 14 hours, 10 mL of isopropyl alcohol was added to the reaction mixture at 65° C., stirred for 1 hour at 50° C. followed by the addition of 12.6 mL of DI water. After 5 minutes, 2 mL ammonia (30% aqueous solution) (0.029 mols) was added and the reaction was stirred for 1 hour at 32° C. to provide the ammonium salt of the resulting polyfluoropolyether phosphate of formula (I) wherein j, q and r were each 1, $R_f$ was $C_3F_7$. $^{31}P$ NMR of the final product showed 46.6 mol % bis(fluoroalkyl)phosphate (x=2) 34.6 mol % fluoroalkylphosphate (x=1) and minor amounts of several other components including phosphate.

A penetrating solution was prepared containing a fluorine concentration of 0.8% fluorine by weight and was applied to limestone, saltillo and granite substrates as described in Test Methods 6 and 7. The substrate samples and untreated controls were tested for water repellency and oil repellency using Test Method 6 and stain resistance according to Test Method 7. The test results are shown in Tables 6, 7 and 8. The product of this example was also tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Tables 13A and 13B.

Example 5

Phosphorous pentoxide (1.11 g) (0.008 mols) was added to 5 g (0.018 mols) of $C_2F_5OCF_2CF_2CH_2CH_2OH$ prepared as in Example 2 at 85° C. and reaction was heated to 100° C. After 14 hours, 6 mL of isopropyl alcohol was added to the reaction mixture at 65° C., stirred for 1 hour at 50° C. followed by the addition of 7.6 mL of DI water. After 5 minutes, 1.2 mL ammonia (30% aqueous solution) (0.017 mols) was added and the reaction was stirred for 1 hour at 32° C. to provide the ammonium salt of the resulting polyfluoropolyether phosphate of formula (I) wherein j, q and r were each 1, and $R_f$ was $C_2F_5$. $^{31}P$ NMR of the final product showed 47.5 mol % bis(fluoroalkyl)phosphate (x=2) 30.1 mol % fluoroalkylphosphate (x=1) and minor amounts of several other components including phosphate.

A penetrating solution was prepared containing a fluorine concentration of 0.8% fluorine by weight and was applied to limestone, saltillo and granite substrates as described in Test Methods 6 and 7. The substrate samples and untreated controls were tested for water repellency and oil repellency using Test Method 6 and stain resistance according to Test Method 7. The test results are shown in Tables 6, 7 and 8. The product of this example was also tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Example 6

Phosphorous pentoxide (1.34 g) (0.0095 mols) was added to 5 g (0.022 mols) of $CF_3OCF_2CF_2CH_2CH_2OH$ prepared as in Example 3 at 85° C. and reaction was heated to 100° C. After 14 hours, 7.1 mL of isopropyl alcohol was added to the reaction mixture at 65° C., stirred for 1 hour at 50° C. followed by the addition of 9 mL of DI water. After 5 minutes, 1.4 mL (0.021 mols) ammonia (30% aqueous solution) was added and the reaction was stirred for 1 hour at 32° C. to provide the ammonium salt of the resulting polyfluoropolyether phosphate of formula (I) wherein j, q and r were each 1, $R_f$ was $CF_3$. $^{31}P$ NMR of the final product showed 45.5 mol % bis(fluoroalkyl)phosphate (x=2) 30.5 mol % fluoroalkylphosphate (x=1) and minor amounts of several other components including phosphate.

A penetrating solution was prepared containing a fluorine concentration of 0.8% fluorine by weight and was applied to limestone, saltillo and granite substrates as described in Test Methods 6 and 7. The substrate samples and untreated controls were tested for water repellency and oil repellency using Test Method 6 and stain resistance according to Test Method 7. The test results are shown in Tables 6, 7 and 8. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

TABLE 6

Tests Results on Saltillo

| | Example 4 | Example 5 | Example 6 | Control |
|---|---|---|---|---|
| % F in solution | 0.8 | 0.8 | 0.8 | 0 |
| Amount Applied (g/m$^2$) | 1.12 | 1.17 | 1.14 | 0 |
| Food stains | | | | |
| Coke | 1 | 1 | 0 | 0 |
| Mustard | 2 | 3 | 3 | 3 |
| Ketchup | 1 | 1 | 1 | 2 |
| Grape juice | 3 | 1 | 3 | 1 |
| Italian dressing | 2 | 1 | 2 | 4 |
| Coffee | 3 | 3 | 2 | 1 |
| Lemon Juice | 1 | 2 | 2 | 3 |
| Motor Oil | 1 | 2 | 1 | 4 |
| Canola Oil | 2 | 2 | 2 | 4 |
| Bacon Grease | 2 | 2 | 2 | 4 |
| Total | 18 | 18 | 18 | 26 |
| Water Beading | 3/4 | 3 | 2/3 | 0 |
| Oil Beading | 4 | 4 | 4 | 0 |

TABLE 7

Tests Results on Limestone

| | Example 4 | Example 5 | Example 6 | Control |
|---|---|---|---|---|
| % F in solution | 0.8 | 0.8 | 0.8 | 0 |
| Amount Applied (g/m$^2$) | 0.5 | 0.48 | 0.48 | 0 |
| Food stains | | | | |
| Coke | 1 | 0 | 2 | 2 |
| Mustard | 3 | 4 | 4 | 3 |
| Ketchup | 2 | 3 | 2 | 3 |
| Grape juice | 2 | 1 | 1 | 2 |
| Italian dressing | 1 | 2 | 2 | 4 |
| Coffee | 1 | 2 | 2 | 3 |
| Lemon Juice | 4 | 4 | 4 | 4 |
| Motor Oil | 0 | 1 | 0 | 4 |
| Canola Oil | 0 | 0 | 0 | 4 |
| Bacon Grease | 0 | 0 | 0 | 4 |
| Total | 14 | 17 | 17 | 33 |
| Water Beading | 4 | 4 | 3 | 1 |
| Oil Beading | 3/4 | 4 | 4 | 1 |

TABLE 8

Tests Results on Granite

| | Example | | | |
|---|---|---|---|---|
| | 4 | 5 | 6 | Control |
| % F in soln | 0.8 | 0.8 | 0.8 | 0 |
| Amt. Applied (g/m$^2$) | 0.35 | 0.41 | 0.39 | 0 |
| Food stains | | | | |
| Coke | 0 | 0 | 0 | 2 |
| Mustard | 0 | 0 | 0 | 3 |
| Ketchup | 0 | 0 | 0 | 2 |
| Grape juice | 0 | 0 | 0 | 3 |
| Italian dressing | 0 | 0 | 0 | 3 |
| Coffee | 0 | 0 | 0 | 3 |
| Lemon Juice | 0 | 0 | 0 | 2 |
| Motor Oil | 0 | 0 | 0 | 3 |
| Canola Oil | 0 | 0 | 0 | 3 |
| Bacon Grease | 0 | 0 | 0 | 3 |
| Total | 0 | 0 | 0 | 27 |
| Water Beading | 2/3 | 2 | 3 | 1 |
| Oil Beading | 3 | 3 | 3 | 2 |

The data in Tables 6, 7 and 8 demonstrates that Examples 4, 5 and 6 of the present invention provided a significant improvement in overall stain resistance versus untreated control for limestone, saltillo and granite substrates for a variety of food stains. Resistance to both oil and water based stains was demonstrated on a variety of substrates, thus demonstrating the efficacy as a hard porous surface protective sealer. The data also demonstrates that the Examples 4, 5 and 6 provided significant improvement to water and oil repellency.

Example 7

Phosphorous pentoxide (0.95 g) (0.0067 mols) was added to 5 g (0.015 mols) of $C_3F_7OCF_2CF_2CH_2CH_2OH$ prepared as in Example 1 at 85° C. and reaction was heated to 105° C. After 14 hours, 12.5 g of ethylene glycol (EG) was added to the reaction mixture at 95° C., stirred for 25 minutes, followed by the addition of TERGITOL 15-S-9 available from Sigma Aldrich, St. Louis, Mo. (1.16 g) at 86° C. After 10 minutes, 0.95 mL (0.0153 mols) ammonia (30% aqueous solution) was added and the reaction was stirred for 10 minutes at 70° C. Finally 30 mL water was added and the reaction was stirred at 70° C. for 1 hour, and the 1.3 mL ammonia (30% aqueous solution) was injected to adjust pH to 9.8 to provide the ammonium salt of the resulting polyfluoropolyether phosphate of formula (I) wherein j, q and r were each 1, and $R_f$ was $C_3F_7$.

The product of this example was tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Example 8

Phosphorous pentoxide (1.15 g) (0.0081 mols) was added to 5 g (0.018 mols) of $C_2F_5OCF_2CF_2CH_2CH_2OH$ prepared as in Example 2 at 85° C. and reaction was heated to 105° C. After 14 hours, 15 g of ethylene glycol was added to the reaction mixture at 95° C., stirred for 25 minutes, followed by the addition of TERGITOL 15-S-9 available from Sigma Aldrich, St. Louis, Mo. (1.37 g) at 86° C. After 10 minutes, 1.14 mL (0.018 mols) ammonia (30% aqueous solution) was added and the reaction was stirred for 10 minutes at 70° C. Finally 36 mL water was added and the reaction was stirred at 70° C. for 1 hour, and the 1.6 mL ammonia (30° A) aqueous solution) was injected to adjust pH to 9.8 to provide the ammonium salt of the resulting polyfluoropolyether phosphate of formula (I) wherein j, q and r were each 1, $R_f$ was $C_2F_5$.

The product of this example was tested for surface tension according to Test Method 3. The resulting data is in Table 9. The product of this example was added to semi-gloss latex paint, high gloss latex paint, and matte latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Example 9

Phosphorous pentoxide (1.41 g) (0.001 mols) was added to 5 g (0.022 mols) of $CF_3OCF_2CF_2CH_2CH_2OH$ prepared as in Example 3 at 85° C. and reaction was heated to 105° C. After 14 hours, 18.32 g of ethylene glycol was added to the reaction mixture at 95° C., stirred for 25 minutes, followed by the addition of TERGITOL 15-S-9 available from Sigma Aldrich, St. Louis, Mo. (1.16 g) at 86° C. After 10 minutes, 1.4 mL (0.022 mols) ammonia (30% aqueous solution) was added and the reaction was stirred for 10 minutes at 70° C. Finally 43 mL water was added and the reaction was stirred at 70° C. for 1 hour, and the 3.0 mL ammonia (30% aqueous solution) was injected to adjust pH to 9.8 to provide the ammonium salt of the resulting polyfluoropolyether phosphate of formula (I) wherein j, q and r were each 1, $R_f$ was $CF_3$.

The product of this example was added to semi-gloss latex paint, and high gloss latex paint in an amount of 0.3% by weight. The contact angle was measured using Test Method 4 and the resulting data is in Tables 11 and 12. Resistance to blocking was measured according to Test Method 2 with results in Table 10. The product of this example was added to semi-gloss latex paint and matte latex paint in an amount of 0.1% by weight. Open time extension was measured using Test Method 5 with the resulting data in Table 13A.

Comparative Example B

The procedure of Example 4 was employed, but using as the fluorochemical a perfluoroalkylethyl alcohol mixture of the formula $F(CF_2)_aCH_2CH_2OH$, wherein a ranged from 6 to 14, and was predominately 6, 8, and 10. The typical mixture was as follows: 27% to 37% of a=6, 28% to 32% of a=8, 14% to 20% of a=10, 8% to 13% of a=12, and 3% to 6% of a=14. The product was added to semi-gloss latex paint and high gloss latex paint in an amount of 0.03% by weight and tested for resistance to blocking using Test Method 2. Results are in Table 10. The product of this example was added to semi-gloss latex paint and matte latex paint in an amount of 0.1% by weight. Open time extension was measured using Test Method 5 with the resulting data in Table 13A.

Comparative Example C

The procedure of Example 7 was employed, but using as the fluorochemical a perfluoroalkylethyl alcohol mixture of the formula $F(CF_2)_aCH_2CH_2OH$, wherein a ranged from 6 to 14, and was predominately 6, 8, and 10. The typical mixture was as follows: 27% to 37% of a=6, 28% to 32% of a=8, 14% to 20% of a=10, 8% to 13% of a=12, and 3% to 6% of a=14. The product was added to semi-gloss latex paint and high gloss latex paint in an amount of 0.03% by weight and tested for resistance to blocking using Test Method 2. Results are in Table 10. The product of this example was added to semi-gloss latex paint and matte latex paint in an amount of 0.1% by weight. Open time extension was measured using Test Method 5 with the resulting data in Table 13A.

The data in Table 10 demonstrates that excellent resistance to blocking was obtained from the examples of the present invention compared to Comparative Examples B and C.

TABLE 11

Advancing Contact Angle in Semi-Gloss Latex Paint

| Example* | Hexadecane |
| --- | --- |
| Control | 28.07 |
| 1 | 76.13 |
| 4 | 75.10 |
| 7 | 77.03 |
| 2 | 76.80 |
| 5 | 77.20 |
| 8 | 77.23 |
| 3 | 73.47 |
| 6 | 72.93 |
| 9 | 72.20 |

*Example added to paint at 0.03% by weight based on solids of the additive in the paint

TABLE 9

Surface Tension (dynes/cm)

| Example* | 0.000% | 0.001% | 0.005% | 0.010% | 0.050% | 0.100% | 0.200% | 0.500% |
| --- | --- | --- | --- | --- | --- | --- | --- | --- |
| 1 | 72.7 | 51.0 | 32.3 | 25.6 | 15.7 | 15.6 | 15.6 | 15.6 |
| 4 | 74.7 | 50.8 | 34.5 | 29.1 | 21.1 | 20.8 | 19.8 | 18.3 |
| 7 | 74.9 | 39.7 | 28.4 | 22.5 | 20.5 | 20.2 | 19.6 | 18.8 |
| 2 | 75.5 | 55.9 | 42.1 | 36.4 | 25.9 | 19.0 | 15.5 | 15.4 |
| 5 | 74.6 | 63.7 | 50.5 | 44.4 | 26.7 | 15.8 | 16.3 | 15.7 |
| 8 | 73.3 | 50.0 | 40.0 | 33.7 | 23.0 | 19.2 | 17.4 | 17.5 |

*Example was added to deionized water by weight based on solids of the additive in the paint.
*Standard Deviation <1 dynes/cm
*Temperature 25° C.

Normal surface tension of deionized water is 72 dyne/cm (shown in Table 9 as 0.000%). When each Example was added at a specified rate, the surface tension of each aqueous solution was reduced significantly. Better performance was obtained at higher levels. According to the results from these tests, excellent surface tension reduction was seen from all Examples of the present invention tested.

TABLE 10

Resistance to Blocking in Semi-Gloss Latex Paint

| Example* | Blocking Rating** | Fluorine (micrograms/g) |
| --- | --- | --- |
| Control | 0.7 | 5 |
| 4 | 9.0 | 165 |
| 7 | 9.0 | 137 |
| 1 | 9.0 | 134 |
| 5 | 8.0 | 154 |
| 8 | 9.0 | 126 |
| 2 | 9.0 | 123 |
| 6 | 6.7 | 70 |
| 9 | 6.0 | 119 |
| 3 | 7.3 | 54 |
| Comparative Example B | 5.0 | 153 |
| Comparative Example C | 5.7 | 155 |

*Example was added to paint at 0.03% based on solids by weight based on solids of the additive in the paint
**Average of 3 replicates

TABLE 12

Advancing Contact Angle in High Gloss Latex Paint

| Example* | Hexadecane |
| --- | --- |
| Control | 5.3 |
| 1 | 60.7 |
| 4 | 68.0 |
| 7 | 63.7 |
| 2 | 54.5 |
| 5 | 61.3 |
| 8 | 52.2 |
| 3 | 30.5 |
| 6 | 36.0 |
| 9 | 24.9 |

*Example added to paint at 0.03% by weight based on solids of the additive in the paint The data in Tables 11 and 12 show excellent increased hexadecane contact angle for all examples of the present invention compared to the control. The increase in the advancing hexadecane contact angle correlates with improved oil repellency.

TABLE 13A

Semi-Gloss Latex Open-Time Extension

| Example | Open Time Extension (min) | % Extension | Fluorine (ppm) |
|---|---|---|---|
| 1 | 4.0 | 12.9% | 435 |
| 2 | 8.0 | 21.1% | 395 |
| 3 | 14.0 | 25.0% | 168 |
| 4 | 4.0 | 13.3% | 538 |
| 5 | 10.0 | 22.7% | 502 |
| 6 | 16.0 | 25.8% | 222 |
| 7 | 5.0 | 18.5% | 445 |
| 8 | 12.0 | 24.0% | 408 |
| 9 | 18.0 | 26.5% | 385 |
| Comparative Example B | 3 | 8.1% | 498 |
| Comparative Example C | 3 | 8.8% | 505 |

*Example added to paint at 0.1% by weight based on solids of the additive in the paint

TABLE 13B

Matte Latex Open-Time Extension

| Example | Open Time Extension (min) | % Extension | Fluorine (ppm) |
|---|---|---|---|
| 1 | 3.0 | 14.3% | 435 |
| 4 | 2.0 | 8.7% | 538 |

*Example added to paint at 0.1% by weight based on solids of the additive in the paint The data in Tables 13A and 13B demonstrates that adding the Examples of the present invention to conventional paints increased the open time extension versus the same paint with no Example of the present invention added. The Examples 1 to 9 were superior to the Comparative Examples B and C. Also the Examples 1 to 9 contained a lower level of fluorine versus Comparative Examples B and C, yet provided superior open time extension, thus demonstrating increased fluorine efficiency.

What is claimed is:

1. A method of providing water repellency, oil repellency and stain resistance to a substrate comprising contacting the substrate with a composition comprising one or more compounds of formula (I) or (II):

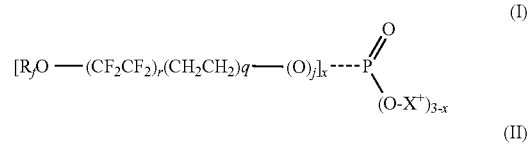
(I)

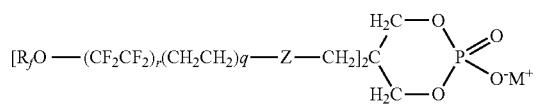
(II)

wherein:
$R_f$ is a linear perfluoroalkyl having 1 to 7 carbon atoms, optionally interrupted by one to three oxygen atoms,
r and q are each independently an integer of 1 to 3,
j is 0 or 1, or a mixture thereof,
x is from about 1 to about 2,
Z is —O—, —S—, or —NR—,
R is hydrogen or an alkyl group containing 1 to 4 carbon atoms
X is hydrogen or M, and
M is an ammonium ion, an alkali metal ion, or an alkanolammonium ion.

2. A method of providing resistance to blocking, open time extension, and oil repellency to a substrate having deposited thereon a coating composition comprising adding to the coating composition prior to deposition on the substrate a composition comprising one or more compounds of formula (I) or (II):

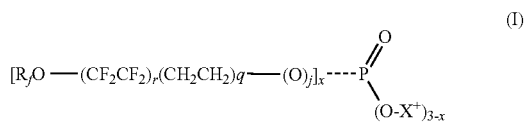
(I)

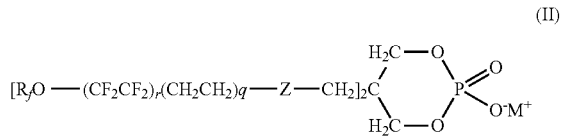
(II)

wherein:
$R_f$ is a linear perfluoroalkyl having 1 to 7 carbon atoms, optionally interrupted by one to three oxygen atoms,
r and q are each independently an integer of 1 to 3,
j is 0 or 1, or a mixture thereof,
x is from about 1 to about 2,
Z is —O—, —S—, or —NR—,
R is hydrogen or an alkyl group containing 1 to 4 carbon atoms
X is hydrogen or M, and
M is an ammonium ion, an alkali metal ion, or an alkanolammonium ion.

3. The method of claim 2 wherein the coating composition is an alkyd coating, Type I urethane coating, unsaturated polyester coating or water dispersed coating.

4. The method of claim 1 or 2 wherein $R_f$ has 4 to 6 carbon atoms, and r, q, and j are each 1.

5. The method of claim 1 or 2 wherein M is an ammonium or an alkanolammonium ion.

6. A substrate treated according to the method of claim 1 or 2.

7. The substrate of claim 6 comprising a fibrous substrate or a hard surface.

8. The substrate of claim 7 which is wood, paper or leather.

9. The substrate of claim 7 which is stone, masonry, concrete, unglazed tile, brick, porous clay, granite, limestone, grout, mortar, marble, wood, gypsum board, terrazzo, glass, or composite materials.

* * * * *